United States Patent
Long et al.

(10) Patent No.: US 8,687,188 B2
(45) Date of Patent: Apr. 1, 2014

(54) METALLIC NANOPARTICLES AND METHODS FOR THEIR PREPARATION AND USE

(75) Inventors: Yitao Long, Shanghai (CN); Dawei Li, Shanghai (CN); Lulu Qu, Shanghai (CN); Wenlei Zhai, Shanghai (CN); Jinqun Xue, Shanghai (CN); Wei Song, Shanghai (CN)

(73) Assignee: East China University of Science and Technology, Shanghai (CN)

( * ) Notice: Subject to any disclaimer, the term of this patent is extended or adjusted under 35 U.S.C. 154(b) by 0 days.

(21) Appl. No.: 13/811,609

(22) PCT Filed: Sep. 22, 2011

(86) PCT No.: PCT/CN2011/080034
§ 371 (c)(1),
(2), (4) Date: Jan. 22, 2013

(87) PCT Pub. No.: WO2013/040782
PCT Pub. Date: Mar. 28, 2013

(65) Prior Publication Data
US 2013/0286389 A1    Oct. 31, 2013

(51) Int. Cl.
*G01J 3/44* (2006.01)

(52) U.S. Cl.
USPC .......................................................... 356/301

(58) Field of Classification Search
USPC .......................................................... 356/301
See application file for complete search history.

(56) References Cited

U.S. PATENT DOCUMENTS 7,790,286 B2    9/2010    Zhang et al.

| 2004/0174520 A1* | 9/2004 | Premasiri et al. ............. 356/301 |
| 2005/0052645 A1* | 3/2005 | Stewart et al. ................ 356/301 |
| 2005/0079630 A1 | 4/2005 | Lazarenko-Manevich et al. |
| 2005/0208663 A1 | 9/2005 | Natan |
| 2007/0259437 A1* | 11/2007 | Natan et al. ..................... 436/79 |
| 2009/0155811 A1 | 6/2009 | Natan et al. |

FOREIGN PATENT DOCUMENTS

| WO | WO 2008/016375 | 1/2008 |
| WO | WO 2010/075534 | 7/2010 |
| WO | WO 2010/081088 | 7/2010 |

OTHER PUBLICATIONS

Lee et al., "Surface-enhanced Raman sensor for trace chemical detection in water", SPIE, vol. 3857, pp. 76-84.*
Spencer et al., "Surface-enhanced Raman as a Water Monitor for Warfare Agents", SPIE, vol. 4577, pp. 158-165.*
Spencer et al., "Surface-enhanced Raman for Monitoring Toxins in Water", SPIE, vol. 5268, pp. 340-348.*
Banholzer et al., "Rationally Designed Nanostructures for Surface-Enhanced Raman Spectroscopy," Chem. Soc. Rev., 2008, pp. 885-897, vol. 37.
Bell et al., "SERS Enhancement by Aggregated Au Colloids: Effect of Particle Size," Phys. Chem. Chem. Phys., 2009, pp. 7455-7462, vol. 11.

(Continued)

*Primary Examiner* — Kara E Geisel
(74) *Attorney, Agent, or Firm* — Knobbe, Martens, Olson & Bear LLP

(57) ABSTRACT

Provided herein are Raman active particles and methods for their preparation and use. The particles can include a SERS-active material that is at least partially encased within a spherical porous hollow casing. In some embodiments, this can be especially advantageous when employed for water analysis and/or being employed in combination with silica particles.

5 Claims, 6 Drawing Sheets

(56) References Cited

OTHER PUBLICATIONS

Brosseau et al., "Ad-Hoc Surface-Enhanced Raman Spectroscopy Methodologies for the Detection of Artist Dyestuffs: Enhanced Raman Spectroscopy an in Situ on the Fiber Analysis," Anal. Chem., 2009, pp. 3056-3062, vol. 81.

Cantu et al., "Surfactant-Enhanced Partitioning of Nickel and Vanadyl Deoxophylloerythroetioporphyrins from Crude Into Water and Their Analysis Using Surface-Enhanced Resonance Raman Spectroscopy," Envion. Sci. Technol., 2000, pp. 192-198, vol. 34(1).

Carrabba et al., "Feasibility Studies for the Detection of Organic-Surface and Subsurface Water Contaminants by Surface-Enhanced Raman-Spectroscopy on Silver Electrodes," Anal. Chem., 1987, pp. 2559-2563, vol. 59 (21).

Costa et al., "Chemical Analysis of Polycyclic Aromatic Hydrocarbons by Surface-Enhanced Raman Spectroscopy," Talanta, 2006, pp. 1011-1016, vol. 70.

Cui et al., "Synthesis of AgcoreAushell Bimetallic Nanoparticles for Immunoassay Based on Surface-Enhanced Raman Spectroscopy," J. Phys. Chem. B., 2006, pp. 4002-4006, vol. 110.

International Search Report and Written Opinion in International Application No. PCT/CN2011/080034, dated Jun. 28, 2012, filed on Sep. 22, 2011.

Jana et al., "Anisotropic Metal Nanoparticles for Use as Surface-Enhanced Raman Substrates," Adv. Mater., 2007, pp. 1761-1765, vol. 19.

Kocsis et al., "Effect of the Preparation Conditions on the Surface-Enhanced Raman-Spectrometric Identification of Thin-Layer-Chromatographic Spots," J. Chromatogr. A., 1999, pp. 197-202, vol. 845.

Li et al., "Multifunctional Au-Coated TiO2 Nanotube Arrays as Recyclable SERS Substrates for Multifold Organic Pollutants Detection," Advanced Functional Materials, Sep. 9, 2010, pp. 2815-2824, vol. 20 (17).

Li et al., "Shell-Isolated Nanoparticle-Enhanced Raman Spectroscopy," Nature, 2010, pp. 392-395, vol. 464.

Liu et al., "Electrochemically Roughened Palladium Electrodes for Surface-Enhanced Raman Spectroscopy: Methodology, Mechanism, and Application," J. Phys. Chem. C., 2007, pp. 1770-1775, vol. 111.

Lu et al., "Aggregation-Based Fabrication and Assembly of Roughened Composite Metallic Nanoshells: Application in Surface-Enhanced Raman Scattering," Langmuir, 2003, pp. 9490-9493, vol. 19.

Lu et al., "Fabrication of Core-Shell Au-Pt Nanoparticle Film and Its Potential Application as Catalysis and SERS Substrate," J. Mater. Chem., 2004, pp. 1005-1009, vol. 14.

Moskovits, "Surface-Enhanced Raman Spectroscopy," Rev. Mod. Phys, 1985, pp. 783-826, vol. 57(3).

Mulvihill et al., "Surface-Enhanced Raman Spectroscopy for Trace Arsenic Detection in Comtaminated Water," Angew. Chem. Int. Ed., 2008, pp. 6456-6460, vol. 47.

Nie et al., "Probing Single Molecules and Single Nanoparticles by Surface-Enhanced Raman Scattering," Science, 1997, pp. 1102-1106, vol. 275.

Perkin Elmer: Nanomaterials Reference Library: Sorption of hydrophobic organic compounds (HOCs) to natural organic matter . . . and highly specific fluoroimmunoassay system for antigen detection using gold . . . and SERS enhancement by aggregated Au colloids: effect of particle size http://www.perkinelmer.com/pages/010/applications/nanomaterialsreferencelibrary.xhtml; Information was available at website: http://www.perkinelmer.com/pages/010/applications/nanomaterialsreferencelibrary.xhtml, in some form no later than May 2, 2011. While no copy of the website as it existed on May 2, 2011, is in Applicant's possession, Applicant has provided the website that was printed on Oct. 11, 2012.

Ren et al., "Surface-Enhanced Raman Scattering in the Ultraviolet Spectral Region: UV-SERS on Rhodium and Ruthenium Electrodes," J. Am. Chem. Soc., 2003, pp. 9598-9599, vol. 125(32).

Rensishaw Diagnostics; www.d3technologies.co.uk; Information was available at website: www.d3technologies.co.uk, in some form no later than May 2, 2011. While no copy of the website as it existed on May 2, 2011, is in Applicant's possession, Applicant has provided the website that was printed on Jul. 7, 2011.

Roca et al., "Design of a Biocompatible and Optically-Stable Solution-Phase Substrate for SERS Detection," Mater. Res. Soc. Symp. Proc., 2009, 6 pages, vol. 1133.

Ruan et al., "Surface-Enhanced Raman Spectroscopy for Uranium Detection and Analysis in Environmental Samples," Anal. Chim. Acta, 2007, pp. 80-86, vol. 605.

Sanles-Sobrido et al., "Design of SERS-Enhanced, Submicron, Hollow Particles Through Confined Growth of Encapsulated Metal Nanoparticles," J. Am. Chem. Soc., 2009, pp. 2699-2705, vol. 131.

Smith, "Practical Understanding and Use of Surface Enhanced Raman Scattering/Surface Enhanced Resonance Raman Scattering in Chemical and Biological Analysis," Chem. Soc. Rev., 2008, pp. 955-964, vol. 37.

Stiles et al., "Surface-Enhanced Raman Spectroscopy," Annu. Rev. Anal. Chem., 2008, pp. 601-626, vol. 1.

Sutherland et al., "Surface-Enhanced Raman Analysis of Sulfa Drugs on Colloidal Silver Dispersion," Analytical Chemistry, Apr. 1, 1990, pp. 689-693, vol. 62 (7).

Wang et al., "Development of Gold-Silica Composite Nanoparticle Substrates for Perchlorate Detection by Surface-Enhanced Raman Spectroscopy," Analytica Chimica Acta, 2006, pp. 121-126, vol. 567.

Xiang et al., "A Controllable Electrochemical Fabrication of Metallic Electrodes with a Nanometer/Angstrom-Sized Gap Using an Electric Double Layer as Feedback," Angew. Chem. Int. Ed., 2005, pp. 1265-1268, vol. 44.

Zhang et al., "Nanomaterials in pollution trace detection and environmental improvement," Nanotoday, Apr. 2, 2010, pp. 128-142, vol. 5 (2).

Zhang et al., "Ultrastable Substrates for Surface-Enhanced Raman Spectroscopy: $Al_2O_3$ Overlayers Fabricated by Atomic Layer Deposition Yield Improved Anthrax Biomarker Detection," J. Am. Chem. Sos., 2006, pp. 10304-10309, vol. 128.

\* cited by examiner

US 8,687,188 B2

METALLIC NANOPARTICLES AND METHODS FOR THEIR PREPARATION AND USE

CLAIM FOR PRIORITY

This application is the U.S. national phase entry under 35 U.S.C. §371 of PCT/CN2011/080034, filed Sep. 22, 2011, the entire disclosure of which is hereby incorporated by reference herein.

TECHNICAL FIELD

The embodiments herein generally relate to metallic nanoparticles and uses thereof.

BACKGROUND

Surface-enhanced Raman spectroscopy (SERS) technology can provide information on a molecular level that is not readily available to other technologies. SERS can also have advantages such as short test time, low water disturbance, direct in situ analysis, high sensitivity and wide test range. In some situations, SERS does not require complicated pretreatment or a high-purity carrier gas.

Nanoparticles of Ag, Au, and other metals of the first subgroup (including some transition metals) in a SERS active substrate material can effectively strengthen the metal surface plasma resonance, thus enhancing electric field coupling or charge transfer of adsorbed molecules on the substrate surface. This can enhance the Raman response signal of the test object.

SUMMARY

In some embodiments, at least one Raman active particle is provided. The particle can include a SERS-active nanoparticle that is at least partially or fully encased within a spherical porous hollow casing. In some embodiments, this can be especially advantageous when employed for water analysis and/or being employed in combination with silica particles.

In some embodiments, devices and/or compositions are provided. The device can include at least one Raman active particle including a SERS-active nanoparticle that is at least partially or fully encased within a spherical porous hollow casing, combined with thin-layer chromatographic grade silica gel particles. The Raman active particle can be mixed in with the thin-layer chromatographic grade silica gel particles.

In some embodiments, methods of performing Raman spectroscopy are provided. The method can include contacting a Raman active particle including a SERS-active nanoparticle that is encased within a spherical porous hollow casing with a sample. The sample can include at least a first impurity and a second impurity. The spherical porous hollow casing can be more permeable to the first impurity than to the second impurity. The method can also include performing surface enhanced Raman spectroscopy on the first impurity.

In some embodiments, methods for obtaining a surface enhanced Raman spectra are provided. The method can include combining at least one Raman active particle including a SERS-active nanoparticle that is at least partially or fully encased within a spherical porous hollow casing with a sample, and performing surface enhanced Raman spectroscopy on the sample using the Raman active particle, thereby obtaining a surface enhanced Raman spectra.

In some embodiments, methods of testing for the presence of an organic compound in water are provided. The method can include creating a mixture by combining a water sample and at least one first Raman active particle including a SERS-active nanoparticle that is at least partially or fully encased within a spherical porous hollow casing, and performing surface enhanced Raman spectroscopy on the mixture using the Raman active particle, thereby obtaining a sample spectra. The method can further include providing a representative spectra of one or more organic compounds mixed with at least one second Raman active particle including a SERS-active nanoparticle that is at least partially or fully encased by a spherical porous hollow casing, and comparing the sample spectra and the representative spectra to determine if the one or more organic compounds is present in the water sample.

In some embodiments, methods of preparing a Raman active particle are provided. The method can include providing a spherical polystyrene particle, adsorbing SERS-active nanoparticle onto the surface of the spherical polystyrene particle by electrostatic adsorption to form a SERS-active nanoparticle, coating the SERS-active nanoparticle with a dissolvable material to form a coated SERS-active nanoparticle, processing the coated SERS-active nanoparticle to form a mesoporous structure, and adding a solvent to dissolve and remove the dissolvable material to obtain a SERS-active nanoparticle within the porous $SiO_2$ porous hollow shell, thereby preparing a Raman active particle.

In some embodiments, methods of preparing a Raman active particle are provided. The method can include providing a hollow spherical $SiO_2$ particle, combining the hollow spherical $SiO_2$ particle with a SERS-active material seed particle such that the seed particle passes into the hollow spherical $SiO_2$ particle and associates with an interior surface of the $SiO_2$ particle, and growing SERS-active nanoparticles on the interior surface, thereby preparing a Raman active particle.

In some embodiments, portable surface enhanced Raman spectroscopy ("SERS") kits are provided. The kit can include a portable Raman spectrometer configured to provide a sample SERS spectra from a sample and at least one Raman active particle having a porous hollow sphere at least partially encasing a SERS-active nanoparticle.

The foregoing summary is illustrative only and is not intended to be in any way limiting. In addition to the illustrative aspects, embodiments, and features described above, further aspects, embodiments, and features will become apparent by reference to the drawings and the following detailed description.

DETAILED DESCRIPTION

Figure 1:
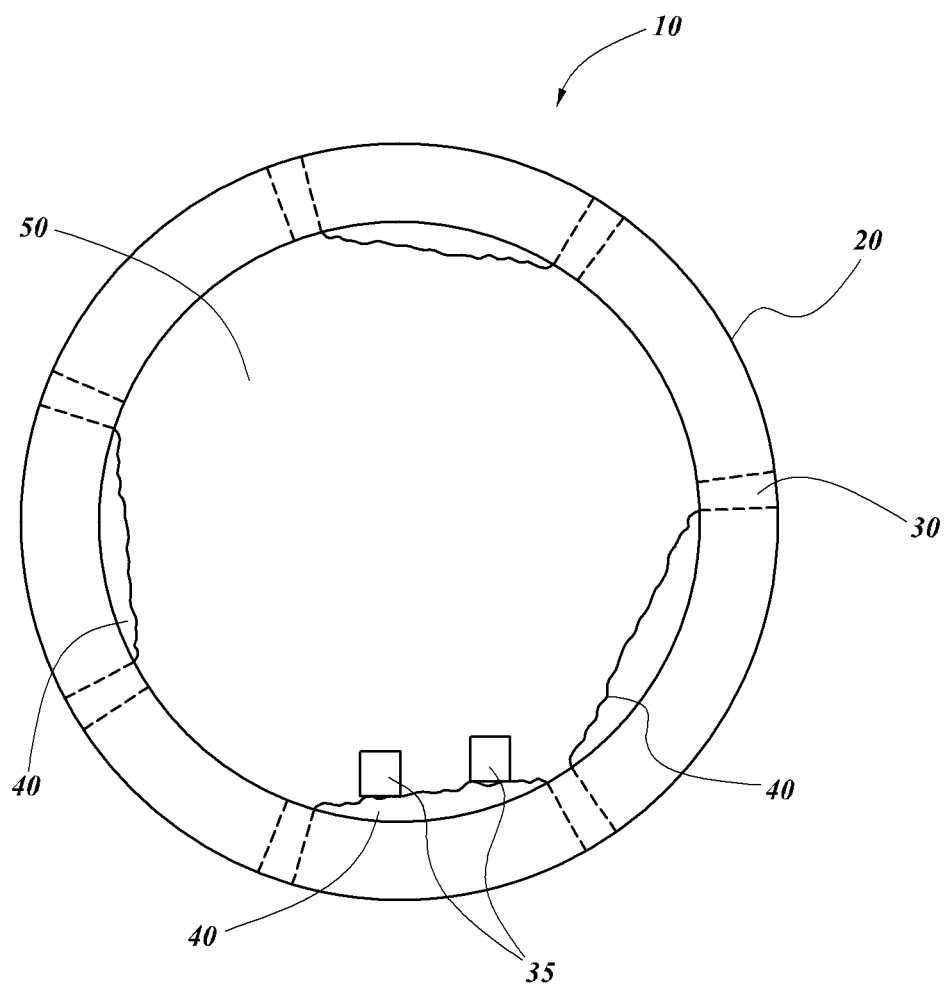
FIG. 1 is a depiction of some embodiments a of Raman active particle.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein.

While current technology can make SERS active substrate materials having either good enhancement effects or with good stability, when SERS technology is used for testing complex samples, it still suffers from problems due to interference of Raman spectrum signals of different materials in (e.g., components of) the sample. To this end, the thin layer chromatography (TLC) separation techniques have been combined with SERS test technology as a combination analysis technology which is used in research on drug analysis, dye testing, bio-analysis, and so on. While TLC-SERS and other techniques can eventually analyze and test comparatively more complex samples, this involves TLC separation followed by enhancement of SERS signals of the sample from the separation point with a metal sol active substrate. Furthermore, it can be difficult to control the degree of aggregation of the sol, and therefore the SERS signals suffer from poor reproducibility. As such, it is difficult to conduct comparative analysis between different spectra.

By taking advantage of the chromatography separation function of silica gel and combining it with metallic nanoparticles to make enhanced SERS substrates, the present disclosure provides, among other things, a way of combining purification aspects and SERS active substrates, thereby providing materials with enhanced Raman spectra and sample separation functions in one composition. It has been discovered that a Raman active particle having a metallic nanoparticle that is at least partially encased within a spherical porous hollow casing can, in some embodiments, address some of the above issues, as well as providing other advantages. Thus, disclosed herein are Raman active particle embodiments involving SERS-active nanoparticles that are at least partially or fully encased within a spherical porous hollow casing.

An example of such a Raman active particle is shown in FIG. 1. In some embodiments, the Raman active particle 10 includes a casing 20. The casing is porous and includes one or more pores 30, which allows access to an interior volume 50 of the casing. Within the casing, there will be at least some amount of a SERS appropriate material, such as gold 40. Pollutants or other analytes to be detected 35 can travel through the pores 30 and interact with the SERS appropriate material 40. It is noted that FIG. 1 is merely a representational depiction of the nanoparticle, and that the casing 20 can be more porous than "shell-like" in some embodiments. In some embodiments, the pores can be of such size that liquid and analytes pass more easily through the outer volume of the casing to the interior volume 50.

In some embodiments, the porous hollow casing is or includes $SiO_2$. In some embodiments, the porous hollow casing is or includes materials such as TiO2, polypropylene, etc.

In some embodiments, the Raman active particle includes at least one organic compound. In some embodiments, the organic compound includes at least one organic pollutant. In some embodiments, the organic pollutant includes a polycyclic aromatic hydrocarbon, an azo dye, pyrocatechol, benzene, benzidine, aniline, substituted aromatic pollutants or mixtures thereof. In some embodiments, the aromatic pollutants are substituted with various groups, such as amino, hydroxyl, carboxyl or halogeno-group. In some embodiments, the Raman active particle includes water. In some embodiments, the water is within the interior volume 50. In some embodiments, the Raman active particle is suspended in water.

In some embodiments, the Raman active particle includes gold, silver, copper, platinum, palladium, or combinations thereof. In some embodiments, the particle includes gold. In some embodiments, the particle does not include gold. In some embodiments, the Raman active particle includes a SERS-active material and/or nanoparticle. The term "SERS-active" denotes that the material is appropriate and/or functional for SERS. Examples of SERS-active materials include, for example, gold, silver, copper, and platinum.

In some embodiments, the diameter of the Raman active particle is about 50 nm to about 1000 nm, for example about 100 nm to about 1000 nm, about 200 nm to about 1000 nm, about 500 nm to about 1000 nm, about 600 nm to about 900 nm, or about 700 nm to about 800 nm. Specific examples of the diameter of the Raman active particle include about 50 nm, about 100 nm, about 200 nm, about 250 nm, about 500 nm, about 750 nm, about 1000 nm, and ranges between any two of these values. In some embodiments, at least one dimension of the Raman active particles can range from 1 to 5000 nanometers, preferably in the range of 5 to 250 nanometers, 10 to 150 nanometers, or 40 to 80 nanometers. Multiple Raman active particles can be substantially the same shape, or can have different shapes. Multiple Raman active particles can have substantially the same size, or can have different sizes.

In some embodiments, the nanoparticle is spherical. In some embodiments, the nanoparticle is random and/or asymmetric, regular or irregular in shape and size. In some embodiments, the hollow casing is configured as a screen or sieve, rather than a wall having occasional pores in it. In some embodiments, the casing merely assists in providing some amount of a filtering function so as to allow for some separation and/or differentiation between various components in a liquid and/or gas sample.

In some embodiments, the diameter of the SERS-active nanoparticle is about 5 nm to about 100 nm, for example about 10 nm to about 90 nm, about 10 nm to about 80 nm, about 10 nm to about 70 nm, about 10 nm to about 60 nm, about 10 nm to about 50 nm, about 20 nm to about 40 nm, or about 25 nm to about 35 nm. Specific examples of diameter include about 10 nm, about 25 nm, about 50 nm, about 75 nm, about 100 nm, and ranges between any two of these values.

In some embodiments, the SERS-active nanoparticle is partially encased within the spherical porous hollow casing. In some embodiments, the SERS-active nanoparticle is fully encased within the spherical porous hollow casing.

Devices/Compositions

In some embodiments, compositions and devices are provided. The composition can include one or more of the SERS-active nanoparticles disclosed herein, combined with one or more components for chromatography (e.g., including thin layer chromatography). In some embodiments, this can provide SERS active substrate devices (or compositions) with enhanced Raman spectrum signals and rapid separation function in one arrangement. In some embodiments, this can be created by mixing one or more of the SERS-active nanoparticles described herein (e.g., the Au-NPs@SiO2 active material) with thin-layer chromatographic grade silica gel particles. In some embodiments, the two can be mixed relatively uniformly. In some embodiments, they can be mixed in a certain proportion (e.g., 1:2 to 2:1 particles to silica gel). In some embodiments, by the use of the enhancement effect of Au nano-particles on the interior wall surface of the nanoparticle in the spherical porous hollow shell, and the adsorption properties of $SiO_2$ surface, an orderly SERS active substrate composition/device is provided that has enhanced Raman spectra and onsite rapid separation function in one location. In some embodiments, this composition can be placed on a glass plate or glass capillary.

In some embodiments, the device can include at least one Raman active particle having a gold nanoparticle that is at least partially encased within a spherical porous hollow casing, and a thin-layer chromatographic grade silica gel particles. The Raman active particle can be mixed in with the thin-layer chromatographic grade silica gel particles.

In some embodiments the device also includes a surface upon which the Raman active particles and the thin-layer chromatographic particles can be positioned. In some embodiments, the surface is a plate or a capillary. In some embodiments, the surface can be any that can support and/or pack the particles without interfering with the laser irradiation during SERS detection. In some embodiments, the plate or capillary is made from glass. In some embodiments, the Raman active particles are evenly distributed across the surface. In other embodiments, the Raman active particles are unevenly distributed, such as in a gradient.

In some embodiments, the ratios of Raman particles to the silica grade particles are 1:10 to 10:1, for example, 1:5 to 5:1, 1:3 to 3:1, or 1:2-2:1.

In some embodiments, the device further includes at least one solvent. In some embodiments the solvent is a TLC appropriate solvent. In some embodiments the solvent is, for example, sodium carboxymethyl cellulose, polyvinyl alcohol, plaster of paris, and/or starch and dextrine.

Methods of Raman Spectroscopy

Figure 2:
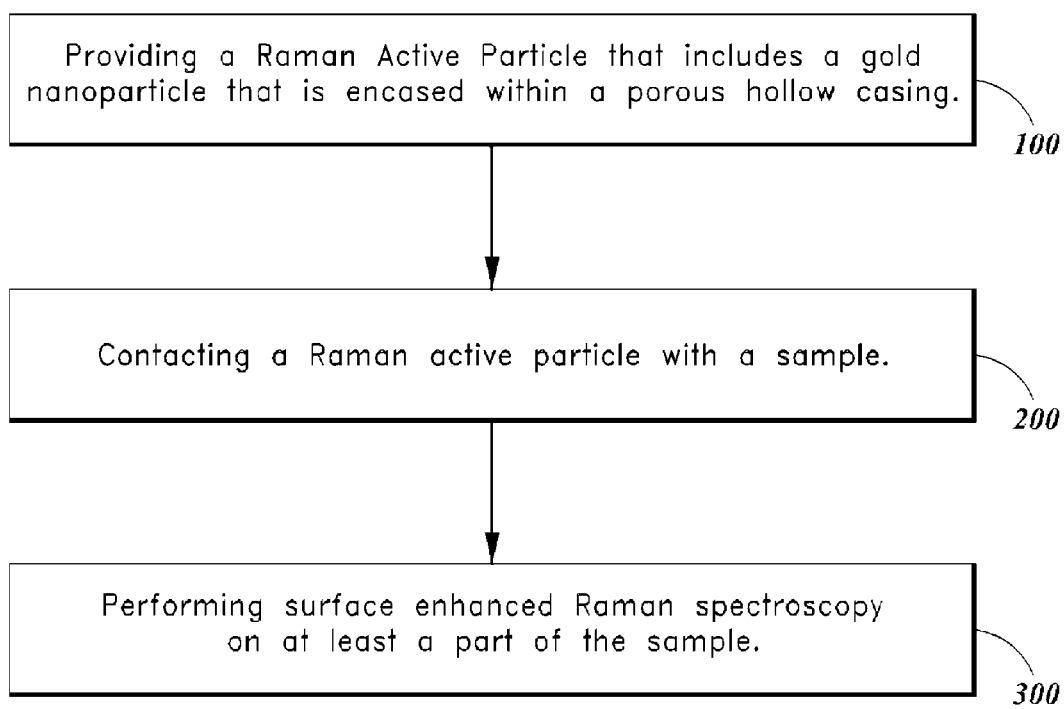
FIG. 2 is a flow chart of some embodiments of using a Raman active particle.

In some embodiments, method of performing Raman spectroscopy are provided. FIG. 2 outlines some embodiments of this method. In some embodiments, the method involves providing a Raman active particle that includes a SERS-active nanoparticle that is encased within a porous hollow casing (block 100). One can then contact a Raman active particle with a sample to be tested (block 200). One can then perform surface enhanced Raman spectroscopy on at least a part of the sample (e.g., whatever part of the sample has entered the porous hollow casing) (block 300). In some embodiments, because of the porous casing, a filtering effect can be achieved such that some components (e.g., analytes) in the sample will enter and contact the metallic region of the Raman active particle before others. In some embodiments, because of the larger size and physical frame work of the Raman active particle, the distribution of the metallic material will be more consistent and appropriate for Raman spectroscopy. In some embodiments, the Raman particle is part of or is mixed with a TLC composition. Thus, further purification and/or separation can be achieved before, during, and/or after the Raman spectra is obtained.

One skilled in the art will appreciate that, for this and other processes and methods disclosed herein, the functions performed in the processes and methods may be implemented in differing order. Furthermore, the outlined steps and operations are only provided as examples, and some of the steps and operations may be optional, combined into fewer steps and operations, or expanded into additional steps and operations without detracting from the essence of the disclosed embodiments.

In some embodiments, the method can include contacting a Raman active particle that includes a SERS-active nanoparticle that is encased within a spherical porous hollow casing with a sample. In some embodiments, the sample includes at least a first impurity and a second impurity. In some embodiments, the spherical porous hollow casing is more permeable to the first impurity than to the second impurity. In some embodiments, the method further includes performing surface enhanced Raman spectroscopy on the first impurity. In some embodiments, a first spectra is obtained on the first impurity, and then a second spectra is later obtained on the second impurity. In some embodiments, the sample includes at least a first analyte and a second analyte. In some embodiments, the spherical porous hollow casing is more permeable to the first analyte than to the second analyte. In some embodiments, the method further includes performing surface enhanced Raman spectroscopy on the first analyte. In some embodiments, a first spectra is obtained on the first analyte, and then a second spectra is later obtained on the second analyte.

In some embodiments, a method for obtaining a surface enhanced Raman spectra is provided. In some embodiments, this includes combining at least one Raman active particle including a gold nanoparticle that is at least partially encased within a spherical porous hollow casing with a sample and performing surface enhanced Raman spectroscopy on the sample using the Raman active particle. In some embodiments, this results in obtaining a surface enhanced Raman spectra. In some embodiments, this spectra can be compared with and/or subtracted from a background spectra and/or spectra of known impurities. In some embodiments, the impurities are organic. In some embodiments, the impurities are present in water. In some embodiments, the impurities are those that are undesired in water.

In some embodiments, the Raman active particle is part of a thin-liquid chromatography plate. In some embodiments, the sample is combined by applying the sample to the thin-liquid chromatography plate.

In some embodiments, the sample is not processed by thin layer chromatography prior to performing the surface enhanced Raman spectroscopy. In some embodiments, there is not a purification process prior to applying the sample to the Raman active particle. In some embodiments, one collects the sample and applies it to the Raman active particle. In some embodiments, one applies the sample to the Raman active particle in the field or outside of a laboratory environment.

In some embodiments, the method includes the step of collecting the sample from a water source, wherein the surface enhanced Raman spectroscopy is performed without a preceding purification process of the sample. In some embodiments, the water source is a fresh water, water source. In some embodiments, the water source is a river, water reservoir, or lake. In some embodiments, the water source is a drinking water source. In some embodiments, the liquid is industrial wastewater, sewer system samples, rainfall/runoff, etc. In some embodiments, the sample is an aqueous sample. In some embodiments, the sample is not an aqueous sample. In some embodiments, the sample can be or include a solid sample. In some embodiments, organic compounds can be extracted from the solid sample to form an aqueous analyte for the following SERS detection.

In some embodiments, the method includes the step of collecting the sample from a water source. In some embodiments, the surface enhanced Raman spectroscopy is performed without performing a separate (and/or non-concurrent) thin layer chromatography analysis on the sample.

In some embodiments, a method of testing for the presence of an organic compound in water or other liquid and/or solid is provided. In some embodiments, the sample can start in a gas phase and be condensed into a liquid phase. The method can include creating a mixture by combining a water sample and at least one first Raman active particle including a SERS-active nanoparticle that is at least partially encased within a spherical porous hollow casing. The method can also include performing surface enhanced Raman spectroscopy on the mixture using the Raman active particle, thereby obtaining a sample spectra. The method can also include providing a representative spectra of one or more organic compounds mixed with at least one second Raman active particle including a gold nanoparticle that is at least partially encased by a spherical porous hollow casing. The method can also include comparing the sample spectra and the representative spectra to determine if the one or more organic compounds is present in the water sample.

In some embodiments, the organic compound includes a drug, a dye, a biological molecule, or mixtures thereof.

In some embodiments, the method can detect substituted aromatic pollutant at a concentration of about 0.1 ppm or greater in the water sample.

In some embodiments, the comparing step is executed on a computer. In other embodiments, the comparing step is performed "by eye" by a user or technician.

In some embodiments, the representative spectra is stored on a computer readable media. In some embodiments, the computer is portable. In some embodiments, the computer is a laptop and/or tablet and/or part of a phone. In some embodiments, the computer is located away from where the sample and/or Raman device is, and the data from the sample is sent electronically to the computer for analysis.

In some embodiments, one can use one or more of the disclosed embodiments for onsite and/or rapid testing of organic pollutants in water based on SERS. In some embodiments, by applying the SERS active substrate devices, one can conduct on-site separation of water samples with organic pollutants. When the separation is complete, one can use a portable Raman spectrometer to do an onsite Raman test on the pollutants on the separation potential, and one can use the analysis software disclosed herein to do an on-site (and/or remote) qualitative/semi-quantitative analysis on the test results. In some embodiments, the organic pollutants include polycyclic aromatic hydrocarbon, azo dye, pyrocatechol, benzene, benzidine, aniline, substituted aromatic pollutants or mixtures thereof.

Methods of Preparing

Figure 3:
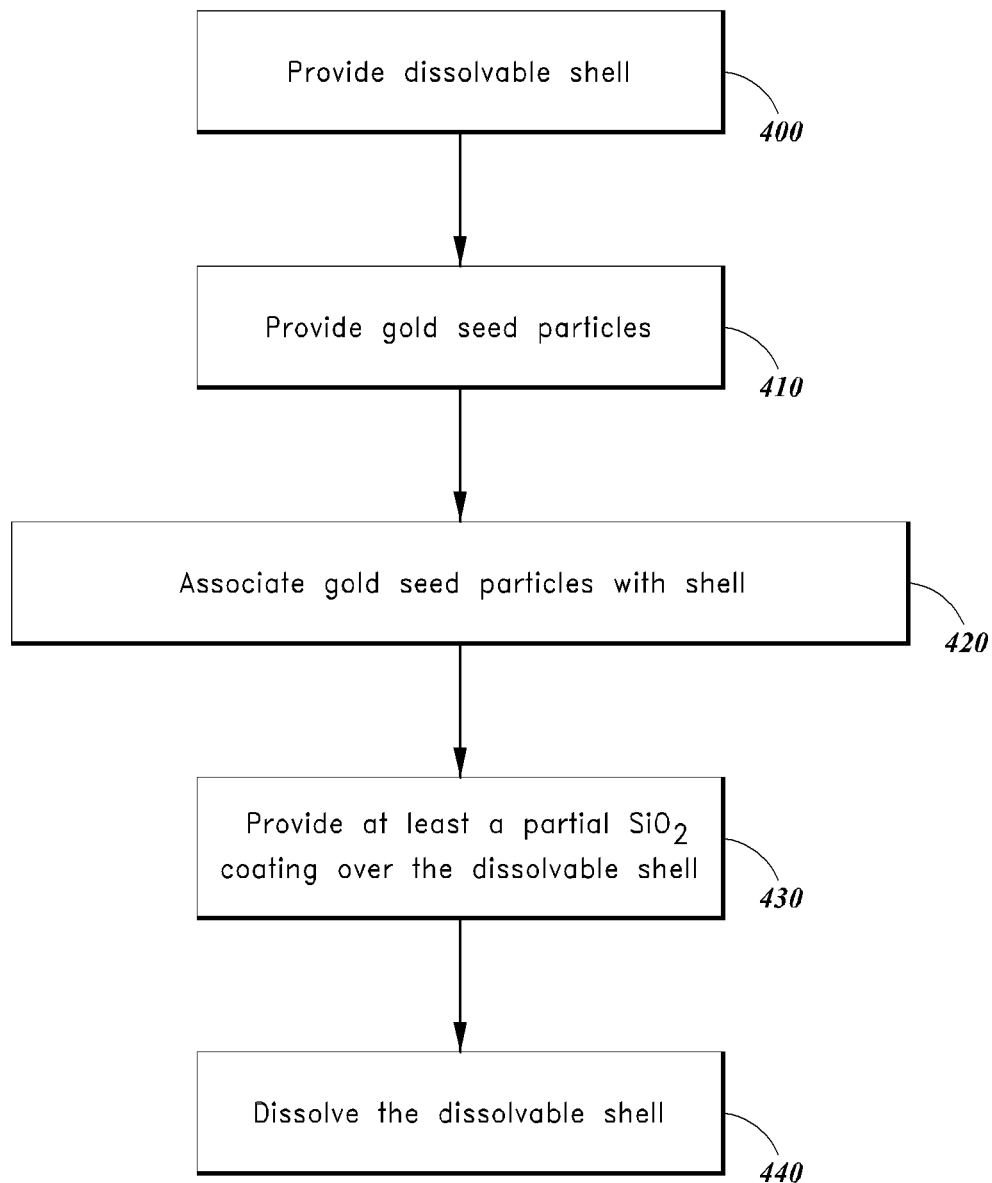
FIG. 3 is a flow chart of some embodiments of making a Raman active particle.

As will be appreciated by one of skill in the art, in light of the present disclosure, there are a variety of ways by which a Raman active particle can be prepared. Some embodiments of these methods are disclosed in FIG. 3. For example, in some embodiments, one can start by providing a dissolvable shell (block 400). One can then provide metallic seed particles (such as gold (block 410)) and then associate the metallic seed particles with the shell (block 420). This can form particles of a PS@Au-seeds structure. One can then process or silanize these particles to form a $SiO_2$ coating over the particles (block 430). This process produces PS@Au-seeds@$SiO_2$ particles having a mesoporous structure. One can then dissolve or remove the dissolvable shell (block 440) by using ethanol or other appropriate solvents, which can pass through the mesopores to contact and dissolve the dissolvable shell.

In some embodiments, the method can include providing a spherical particle of a dissolvable material. In some embodiments, the method can include providing a spherical polystyrene particle. The method can also include adsorbing gold onto the surface of the spherical polystyrene particle by electrostatic adsorption to form a gold nanoparticle. The method can also include coating the gold nanoparticle with a dissolvable material to form a coated gold nanoparticle. One can then process the coated gold nanoparticle to form a mesoporous structure. One can then add a solvent to dissolve and remove the dissolvable material to obtain a gold nanoparticle within the porous $SiO_2$ porous hollow shell, thereby preparing a Raman active particle. In some embodiments, the dissolvable material includes polypyrrolidone and the solvent can include ethanol.

In some embodiments, the method can include providing (e.g., making, obtaining, putting in a container, etc.) a hollow spherical $SiO_2$ particle, combining the hollow spherical $SiO_2$ particle with a SERS-active seed particle such that the gold seed particle passes into the hollow spherical $SiO_2$ particle and associates with at least an interior surface of the $SiO_2$ particle, and growing gold nano-particles on the interior surface, thereby preparing a Raman active particle. In some embodiments, the method can also include performing an in situ catalytic reduction technique. In some embodiments, the gold only associates with the interior of the $SiO_2$ shell. In some embodiments, there is more gold associated with the interior of the $SiO_2$ particle than the exterior of the $SiO_2$ particle. In some embodiments, there is an approximately equal amount of gold associated with the interior and the exterior of the $SiO_2$ particle. In some embodiments, there is more gold associated with the exterior of the $SiO_2$ particle. In some embodiments, the gold is associated with the interior of the $SiO_2$ shell because there are no or fewer gold seeds on the exterior of the particle. When gold is associated with both the interior and the exterior of $SiO_2$ shell, the exterior gold nano-particles may not need to be removed if the detection properties are not hindered.

In some embodiments, a Raman active particle can be made using a polystyrene sphere ("PS") of a sub-micron level as a template. By using electrostatic adsorption onto the surface, the seed of the Au nano-particles can be adsorbed onto the electrolyte surface. This can form particles of a PS@Au-seeds structure. In some embodiments, one can use polypyrrolidone and/or other reagents to coat the PS@Au-seeds particles. In some embodiments, one performs a silanization treatment to obtain PS@Au-seeds@$SiO_2$ particles of a mesoporous structure. In some embodiments, one can then use ethanol and/or other solvents on the particles and, through the mesopores, dissolve and remove the internal polystyrene sphere. This can provide Au-seeds@$SiO_2$ hollow spherical particles.

In some embodiments, one can immerse a hollow sphere material in a SERS-active material (e.g., Au) ion solution and allow the Au ions to enter the hollow part through the mesopores. In some embodiments, one can use Au seeds on the interior wall surface of the $SiO_2$ shell and use an in situ seed catalytic reduction technique and an Au ion solution as raw materials such that Au nano-particles are grown in an orderly sequence on its interior wall surface. One can thereby obtain a sub-micron level Au-NPs@SiO$_2$ porous hollow sphere active substrate.

Kits and Systems

In some embodiments, a portable surface enhanced Raman spectroscopy ("SERS") kit is provided. The kit can include a portable Raman spectrometer configured to provide a sample SERS spectra from a sample. The kit can also include at least one Raman active particle including a porous hollow sphere that at least partially encases a SERS-active nanoparticle.

In some embodiments, a computer readable memory is provided as an additional component of the kit. In some embodiments, the media can include data regarding a representative SERS spectra for at least one organic compound. In some embodiments, the organic compound includes an organic pollutant (such as polycyclic aromatic hydrocarbon, an azo dye, pyrocatechol, benzene, benzidine, aniline, substituted aromatic pollutants or mixtures thereof). In some embodiments, the memory includes data that was obtained on the same type of portable Raman spectrometer and/or using a same type of Raman active particle and/or same amount of TLC silica composition. In some embodiments, the data includes data that was obtained by using at least one Raman active particle including a porous hollow sphere at least partially encasing a gold nanoparticle.

In some embodiments, there can also be a computer readable memory having software configured to compare the representative SERS spectra to the sample SERS spectra and to display similarities and difference between the representative SERS spectra and the sample SERS spectra.

In some embodiments, a SERS spectral database and analysis software of organic pollutants in water can be provided. In some embodiments, one can perform SERS spectrum collection on water samples with such different representative organic pollutants, such as (but not limited to) benzene, polycyclic aromatic hydrocarbons, azo dyes, etc. One can also perform the SERS analysis on the organic pollutants at different concentrations. This can establish qualitative and semi-quantitative analysis results for SERS spectra of the representative organic pollutants in water. In some embodiments, a corresponding mathematical model can be established, and analysis software that can be used in onsite test of organic pollutants in water can be compiled.

In some embodiments, a system for detecting an analyte (such as a pollutant) includes an information processing system. An exemplary information processing system can incorporate a computer that includes a bus for communicating information and a processor for processing information. In some embodiments, the processor is selected from the Pentium® family of processors, including without limitation the Pentium® II family, the Pentium® III family and the Pentium® 4 family of processors available from Intel Corp. (Santa Clara, Calif.). In some embodiments, the processor may be a Celeron®, an Itanium®, or a Pentium Xeon® processor (Intel Corp., Santa Clara, Calif.). In some embodiments, the processor may be based on Intel® architecture, such as Intel® IA-32 or Intel® IA-64 architecture. Alternatively, other processors may be used. The information processing and control system can further include any peripheral devices known in the art, such as memory, display, keyboard and/or other devices.

In some embodiments, the detection unit can be operably coupled to the information processing system. Data from the detection unit may be processed by the processor and data stored in memory. Data on emission profiles for various Raman labels may also be stored in memory. The processor may compare the emission spectra from the sample in the flow path and/or flow-through cell to identify the Raman-active organic compound. The processor can analyze the data from the detection unit to determine, for example, the pollutant bound by the nanoparticle employed by the methods. The information processing system may also perform standard procedures such as subtraction of background signals.

While certain methods can be performed under the control of a programmed processor, in alternative embodiments, the methods may be fully or partially implemented by any programmable or hardcoded logic, such as Field Programmable Gate Arrays (FPGAs), TTL logic, or Application Specific Integrated Circuits (ASICs). Additionally, the disclosed methods may be performed by any combination of programmed general purpose computer components and/or custom hardware components.

Following the data gathering operation, the data can be reported to a data analysis operation. To facilitate the analysis operation, the data obtained by the detection unit will typically be analyzed using a digital computer such as that described above. Typically, the computer will be appropriately programmed for receipt and storage of the data from the detection unit as well as for analysis and reporting of the data gathered. In some embodiments, custom designed software packages can be used to analyze the data obtained from the detection unit. In some embodiments, data analysis can be performed, using an information processing system and publicly available software packages.

Some embodiments presented herein can achieve on-site separation and high stability test of different types of organic pollutants in water samples through the preparation of a new sub-micron level Au-NPs@SiO2 porous hollow sphere active substrate, which has the SERS activity and is capable of on-site rapid separation, manufacture of the corresponding SERS active substrate devices, in combination with a portable Raman spectrometer; in combination with a SERS spectral database and analysis software of organic pollutants based on the substrate devices. This can provide for an automatic comparison and analysis of the test results can be completed so that on-site rapid qualitative and semi quantitative analysis of organic pollutants in water can be achieved.

Additional Embodiments

In some embodiments, the Raman spectrometer can be part of a detection unit designed to detect and quantify metallic colloids of the present invention by Raman spectroscopy. Variations on surface enhanced Raman spectroscopy (SERS), surface enhanced resonance Raman spectroscopy (SERRS) and coherent anti-Stokes Raman spectroscopy (CARS) are also known and are included within the present embodiments.

A non-limiting example of a Raman detection includes an excitation beam that is generated by either a frequency doubled Nd:YAG laser at 532 ran wavelength or a frequency doubled Ti:sapphire laser at 365 nm wavelength. Pulsed laser beams or continuous laser beams can be used. The excitation beam passes through confocal optics and a microscope objective, and is focused onto the flow path and/or the flow-through cell. The Raman emission light from the pollutants or analytes adsorbed is collected by the microscope objective and the confocal optics and is coupled to a monochromator for spectral dissociation. The confocal optics includes a combination of dichroic filters, barrier filters, confocal pinholes, lenses, and mirrors for reducing the background signal. Standard full field optics can be used as well as confocal optics. The Raman emission signal is detected by a Raman detector that includes an avalanche photodiode interfaced with a computer for counting and digitization of the signal.

Another example of a Raman detection unit is a Spex Model 1403 double-grating spectrophotometer with a gallium-arsenide photomultiplier tube (RCA Model C31034 or Burle Industries Model C3103402) operated in the single-photon counting mode. The excitation source includes a 514.5 nm line argon-ion laser from SpectraPhysics, Model 166, and a 647.1 nm line of a krypton-ion laser (Innova 70, Coherent).

Alternative excitation sources include a nitrogen laser (Laser Science Inc.) at 337 nm and a helium-cadmium laser (Liconox) at 325 nm, a light emitting diode, an Nd:YLF laser, and/or various ions lasers and/or dye lasers. The excitation beam can be spectrally purified with a bandpass filter (Corion) and may be focused on the flow path and/or flow-through cell using a 6× objective lens (Newport, Model L6X). The objective lens may be used to both excite the analyte and to collect the Raman signal, by using a holographic beam splitter (Kaiser Optical Systems, Inc., Model HB 647-26N18) to produce a right-angle geometry for the excitation beam and the emitted Raman signal. A holographic notch filter (Kaiser Optical Systems, Inc.) can be used to reduce Rayleigh scattered radiation. Alternative Raman detectors include an ISA HR-320 spectrograph equipped with a red-enhanced intensified charge-coupled device (RE-ICCD) detection system (Princeton Instruments). Other types of detectors may be used, such as Fourier-transform spectrographs (based on Michaelson interferometers), charged injection devices, photodiode arrays, InGaAs detectors, electron-multiplied CCD, intensified CCD and/or phototransistor arrays.

Any suitable form or configuration of Raman spectroscopy or related techniques known in the art can be used for detection in the methods herein, including but not limited to normal Raman scattering, resonance Raman scattering, surface enhanced Raman scattering, surface enhanced resonance Raman scattering, coherent anti-Stokes Raman spectroscopy (CARS), stimulated Raman scattering, inverse Raman spectroscopy, stimulated gain Raman spectroscopy, hyper-Raman scattering, molecular optical laser examiner (MOLE) or Raman microprobe or Raman microscopy or confocal Raman microspectrometry, three-dimensional or scanning Raman, Raman saturation spectroscopy, time resolved resonance Raman, Raman decoupling spectroscopy or UV-Raman microscopy.

In some embodiments, the Raman spectrometer can be part of a detection unit designed to detect and quantify nanoparticles by Raman spectroscopy. Methods for detection of Raman labeled analytes, for example nucleotides, using Raman spectroscopy are known in the art. (See, for example, U.S. Pat. Nos. 5,306,403; 6,002,471; and 6,174,677). Variations on surface enhanced Raman spectroscopy (SERS), surface enhanced resonance Raman spectroscopy (SERRS) and coherent anti-Stokes Raman spectroscopy (CARS) have been disclosed.

Any suitable form or configuration of Raman spectroscopy or related techniques known in the art may be used for detection of the nanoparticles disclosed herein, including but not limited to surface enhanced Raman scattering or surface enhanced resonance Raman scattering.

In some embodiments, the particle embodiments presented herein can have a large amount of gold planted on the inner walls of the hollow silica spheres with sub-micron size. In some embodiments, this structure can produce more "hot spots" that improve the SERS response.

In some embodiments, the sub-micron size of the silica spheres of the Raman particles can be similar to that of the commercial silica gel particles, which can make it easier to evenly mix the two kinds of particles and distribute the mixture appropriately across the surface. Thus, in some embodiments, the herein disclosed SERS-active substrates can exert excellent performance both in SERS detection and/or in sample separation.

In some embodiments, one or more of the embodiments provided herein has one or more advantage of the following: simple operation, rapid test, high sensitivity and stability, and wide application, and can be used for sudden water pollution incidents by providing a new technological approach for onsite emergent analysis. In some embodiments, one or more of the embodiments provided herein has one or more advantage of the following: a low cost configuration and application of the test technology which makes it applicable at various levels of environmental monitoring, emergency applications, or routine monitoring of organic pollutants in water.

In some embodiments, compared with the existing SERS active substrate devices either with good enhancement effects or with good stability, the embodiments presented herein can be used in the separation and testing of complex samples and can avoid and or reduce the problem of Raman spectrum signal interference between different substances in the sample. In some embodiments, compared with TLC-SERS and other such techniques, the embodiments provided herein can obtain stable SERS test signals, while avoiding difficulties in controlling the degree of sol aggregation and poor reproducibility of SERS signals and other unfavorable factors. In some embodiments, this provides for a superior comparison of data from different test batches.

The phrase "SERS active material" or "SERS active particle" refers to a material or a particle that produces a surface-enhanced Raman scattering effect. The SERS active material or particle generates surface enhanced Raman signal specific to the analyte molecules when the analyte-particle complexes are excited with a light source as compared to the Raman signal from the analyte alone in the absence of the SERS active material or SERS active particle. The enhanced Raman scattering effect provides an enhanced Raman signal from Raman-active analyte molecules that have been adsorbed onto certain specially-prepared SERS active surfaces. The SERS active surface can be planar, random, or curved (as shown in FIG. 1). Typically, the SERS active surfaces are metal surfaces. Increases in the intensity of Raman signal can be in the order of $10^4$-$10^{14}$ for some systems. SERS active material or particle includes a variety of metals including coinage (Au, Ag, Cu), alkalis (Li, Na, K), Al, Pd and Pt.

As used herein, "Raman-active organic compound" refers to an organic molecule that produces a unique SERS signature in response to excitation by a laser. In some embodiments, Raman-active organic compounds are polycyclic aromatic or heteroaromatic compounds. In some embodiments, the Raman-active organic compound has a molecular weight less than about 300 Daltons. In some embodiments, the compound includes a pollutant. In some embodiments, the pollutant is one found in water.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds, compositions or biological systems, which can, of course, vary. It is also to be understood that the terminology used herein is for the purpose of describing particular embodiments only, and is not intended to be limiting.

In an illustrative embodiment, any of the operations, processes, etc. described herein can be implemented as computer-readable instructions stored on a computer-readable medium. The computer-readable instructions can be executed by a processor of a mobile unit, a network element, and/or any other computing device.

There is little distinction left between hardware and software implementations of aspects of systems; the use of hardware or software is generally (but not always, in that in certain contexts the choice between hardware and software can become significant) a design choice representing cost vs. efficiency tradeoffs. There are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; if flexibility is paramount, the implementer may opt for a mainly software implementation; or, yet again alternatively, the implementer may opt for some combination of hardware, software, and/or firmware.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In one embodiment, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive, a CD, a DVD, a digital tape, a computer memory, etc.; and a transmission type medium such as a digital and/or an analog communication medium (e.g., a fiber optic cable, a waveguide, a wired communications link, a wireless communication link, etc.).

Those skilled in the art will recognize that it is common within the art to describe devices and/or processes in the fashion set forth herein, and thereafter use engineering practices to integrate such described devices and/or processes into data processing systems. That is, at least a portion of the devices and/or processes described herein can be integrated into a data processing system via a reasonable amount of experimentation. Those having skill in the art will recognize that a typical data processing system generally includes one or more of a system unit housing, a video display device, a memory such as volatile and non-volatile memory, processors such as microprocessors and digital signal processors, computational entities such as operating systems, drivers, graphical user interfaces, and applications programs, one or more interaction devices, such as a touch pad or screen, and/or control systems including feedback loops and control motors (e.g., feedback for sensing position and/or velocity; control motors for moving and/or adjusting components and/or quantities). A typical data processing system may be implemented utilizing any suitable commercially available components, such as those typically found in data computing/communication and/or network computing/communication systems.

The herein described subject matter sometimes illustrates different components contained within, or connected with, different other components. It is to be understood that such depicted architectures are merely examples, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled", to each other to achieve the desired functionality, and any two components capable of being so associated can also be viewed as being "operably couplable", to each other to achieve the desired functionality. Specific examples of operably couplable include but are not limited to physically mateable and/or physically interacting components and/or wirelessly interactable and/or wirelessly interacting components and/or logically interacting and/or logically interactable components.

EXAMPLES

Example 1

Method of Preparing SERS Particles

The present example outlines one way of making a SERS particle. One starts with a collection of spherical polystyrene particles with average particle size of 300 nm. Then, 100 mg of spherical polystyrene particles were added into 0.5 mM of gold seed colloid to absorb gold seeds by electrostatic adsorption for 1 h to form gold nanoparticles. The gold nanoparticle is then coated with 2 mL polypyrrolidone to form a coated gold nanoparticle. After 2 h, 500 μL tetraethoxysilane is added to the gold nanoparticle suspension and then processed to form a mesoporous structure. One then adds ethanol to dissolve the polypyrrolidone coating. One then removes the dissolvable material to obtain a gold nanoparticle (average size about 20 nm) within the porous $SiO_2$ porous hollow shell (average size about 320 nm).

Figure 4:
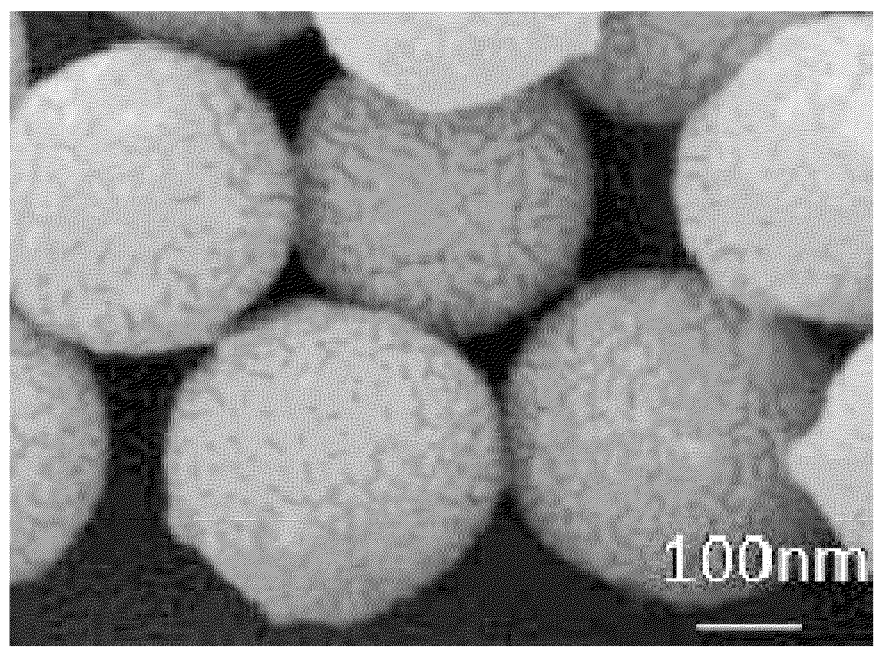
FIG. 4 is a SEM image of some embodiments of a SERS-active nanoparticle.

FIG. 4 depicts a SEM image of the resulting embodiment from the above example of a SERS-active particle.

Example 2

Method of Making SERS Particles

The present example outlines one method of making a SERS particle. One starts with a hollow spherical $SiO_2$ particle. One then combines the hollow spherical $SiO_2$ particle with gold seed particles, allowing the gold seed particles to pass into the hollow spherical $SiO_2$ particle. The gold seed particles will associate with an interior surface of the $SiO_2$ particle. One then grows the gold nano-particles on the interior surface by using an in situ catalytic reduction technique in the presence of a gold ion solution. One can thereby prepare a SERS particle.

Example 3

Method of Using SERS Particles

The present example outlines one way of obtaining a surface enhanced Raman spectra. One first obtains a sample which one wishes to determine the contents of The sample can, optionally, be purified. One then combines the sample with a collection of Raman active particles that have a gold nanoparticle that is at least partially encased within a spherical porous hollow casing. Surface enhanced Raman spectroscopy can then be performed on the combined mixture, which will provide a surface enhanced Raman spectra. The spectra from the experiment will then be compared to spectra from samples with known ingredients, to determine if any of the ingredients from the other samples are also present in the test sample. In the alternative, the sample is not purified, or at least not separately run on TLC, before it comes into contact with the Raman active particle.

Example 4

Method of Testing a Water Sample

The present example outlines a method of testing water samples in the field. One will first obtain a water sample in the field. While still in the field, one then creates a mixture by combining the water sample and a Raman active particle that will include a gold nanoparticle that is at least partially encased within a spherical porous hollow casing. While still in the field, one performs a surface enhanced Raman spectroscopy on the mixture to obtain a sample spectra.

The method can further include providing a representative spectra of one or more organic compounds mixed with at least one second Raman active particle including a gold nanoparticle that is at least partially encased by a spherical porous hollow casing, and comparing the sample spectra and the representative spectra to determine if the one or more organic compounds is present in the water sample.

Example 5

Method of Making SERS Substrate (or Composition)

The present Example outlines a method of making a SERS composition that can provide both enhanced Raman signals and rapid separation. One can start by mixing Au-NPs@SiO2 (average particles size: about 320 nm) with thin-layer chromatographic grade silica gel particles (average particles size: about 300 nm) uniformly and in a 1:2 ratio, using 2 wt % sodium carboxymethylcellulose solution as a solvent. The mixture is then added to a glass plate at to create a SERS substrate to which a sample can be added.

Example 6

Method of Using a SERS Substrate (or Composition)

The present example demonstrates how one can use the product from Example 5 for providing both enhanced Raman signals and rapid separation.

A liquid sample is applied to the product of Example 5. The TLC grade silica particles assists in the separation of various ingredients in the sample concurrently with the interaction of the various ingredients with the Au-NPs@SiO2 active material. Given the combination, SERS spectra and rapid separation are achieved by the use of the composition on the glass plate composition.

Example 7

Method of Using a SERS Substrate (or Composition)

The present example demonstrates how one can use the product from Example 5 for providing both enhanced Raman signals and rapid separation.

A polluted water sample was applied to the product of Example 5. The sample was separated on the product from Example 5 and each of the separated spots were analysed by SERS.

SERS spectra for the four separated spots on the plate are shown in FIGS. 5A-5D. FIG. 5F depicts the separated spots examined and the general setup for the SERS data gathering. Comparing the SEAS spectra from each of the spots with the SERS spectrum library (see, e.g., FIG. 6A-6P), good matches were found between FIGS. 5A, 5B, 5C, 5D and FIGS. 6F, 6C, 6D, and 6A respectively, which correspond to the SERS spectra of chlorobenzene, aniline, benzidine and pyrocatechol, respectively. As such, the mixed water sample was identified was containing chlorobenzene, aniline, benzidine and pyrocatechol.

Figure 5A:
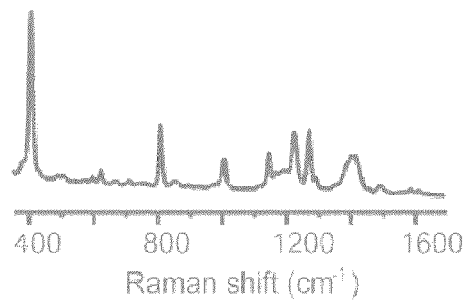
FIG. 5A is a spectra which employed a SERS-active nanoparticle.
Figure 5B:
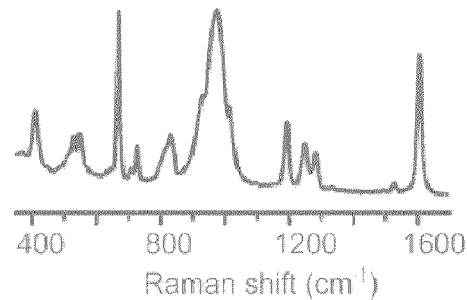
FIG. 5B is a spectra which employed a SERS-active nanoparticle.
Figure 5C:
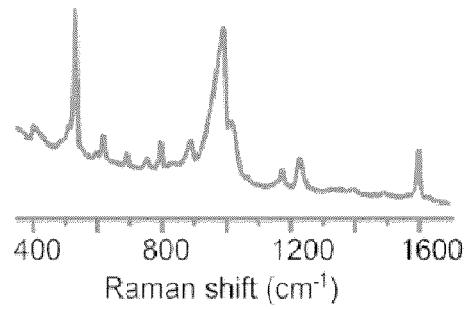
FIG. 5C is a spectra which employed a SERS-active nanoparticle.
Figure 5D:
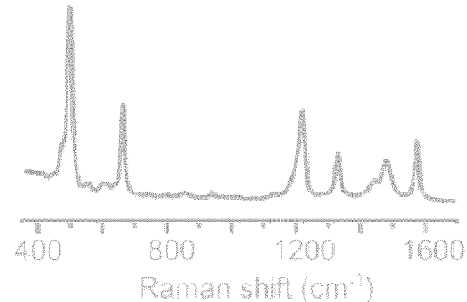
FIG. 5D is a spectra which employed a SERS-active nanoparticle.
Figure 5E:
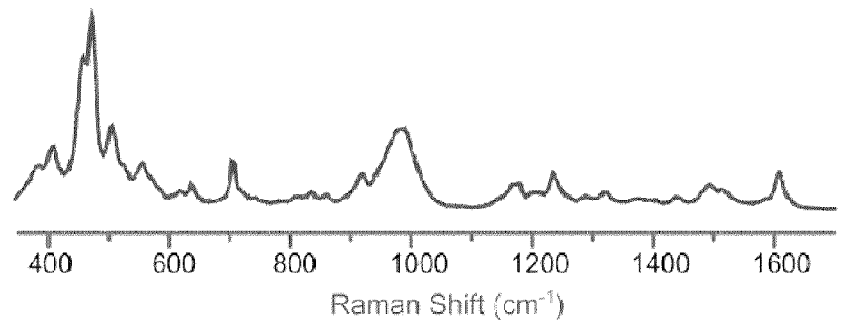
FIG. 5E is a spectra which did not employ a SERS-active nanoparticle, but instead employed a conventional SERS nanoparticle (gold colloid containing spherical gold nanoparticles).
Figure 5F:
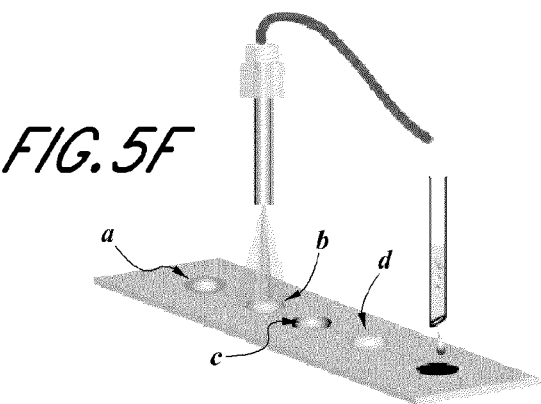
FIG. 5F is a depiction of a set up for detecting various isolated samples on a surface.

To further demonstrate the resolving ability of the present compositions and methods, a SERS spectrum for the polluted water sample was also performed without the SERS-active nanoparticle composition of Example 5, but with a conventional SERs particle (which was a gold colloid which was obtained by chemical reduction of 0.02 wt % chloroauric acid by 1 wt % sodium citrate under boiling condition; the gold colloid contained spherical gold nanoparticles with average size about 70 nm), the results are shown in FIG. 5E). As is clear from the data in FIG. 5E, performing SERS using conventional spherical gold nanoparticles (rather than the use of the product from Example 5) produced results that did not match any SERS spectrum in the library. Thus, without the developed SERS-active nanoparticles, it can be difficult to identify which pollutant is contained in the sample.

Example 8

Method of Developing a SERs Database

The present example outlines how one can develop a portable SERS database. One can use a portable Raman spectroscopy instrument and the nanoparticles disclosed herein to test water mixed with various organic pollutants of interest, including the following: benzene, polycyclic aromatic hydrocarbons, and azo dyes. The SERS analysis of these organic pollutants can be repeated at different concentrations of pollutant, with a SERS spectra being taken for each sample and/or concentration. This will provide a library of qualitative and semi-quantitative SERS spectra of the representative organic pollutants in water. A corresponding mathematical model can then be established. Analysis software employing these data and mathematical models can then be created, which can be used for full onsite testing and analysis of organic pollutants in water.

In some embodiments, the model can be established based on the signal processing technique such as wavelet analysis, and the software can be developed based on the model and the software kit of the commercial Raman spectrometer. In some embodiments, the model and software are used to determine the amounts, positions and height (or integral area) of the peaks in SERS spectra and to match these parameters between the detected spectra of samples and the spectra in SERS database for intelligently deciding the species and concentrations of the compounds in samples.

Example 9

Method of Developing a SERs Database

Figure 6:
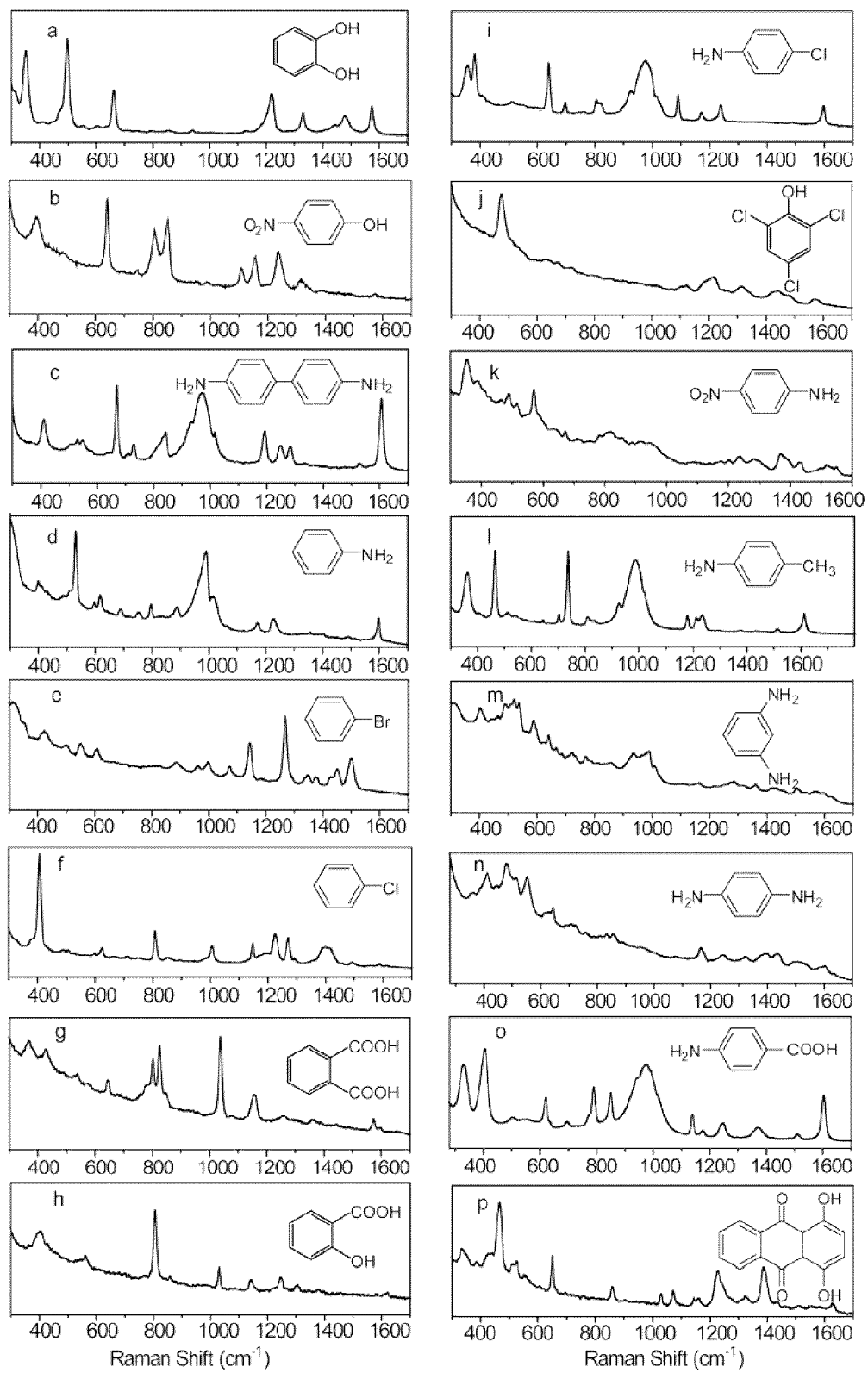
FIGS. 6A-6P depict the SERS spectra of the various compounds identified in each panel, taken using SERS-active nanoparticles.

An example of a library of SERs spectra is shown in FIGS. 6A-6P. FIGS. 6A-6P depict various SERS spectra for the identified compounds in each of the figures. Each of the spectra was obtained by combining the noted chemical (in each panel) with water to form a mixture, adding that mixture to the gold SERS-active particle (from Example 1), and then performing a surface enhanced Raman spectroscopy on the final mixture to obtain the spectra noted in FIGS. 6A-6P.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," and the like include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

From the foregoing, it will be appreciated that various embodiments of the present disclosure have been described herein for purposes of illustration, and that various modifications may be made without departing from the scope and spirit of the present disclosure. Accordingly, the various embodiments disclosed herein are not intended to be limiting, with the true scope and spirit being indicated by the following claims.

What is claimed is:

1. A method of testing for the presence of an organic compound in water, the method comprising:
    creating a mixture by combining a water sample and at least one first Raman active particle comprising a SERS-active nanoparticle that is at least partially encased within a spherical porous hollow casing;
    performing surface enhanced Raman spectroscopy on the mixture using the Raman active particle, thereby obtaining a sample spectra;
    providing a representative spectra of one or more organic compounds mixed with at least one second Raman active particle comprising a SERS-active nanoparticle that is at least partially encased by a spherical porous hollow casing; and comparing the sample spectra and the representative spectra to determine if the one or more organic compounds is present in the water sample.

2. The method of claim 1, wherein the organic compound comprises a drug, a dye, a biological molecule, or mixtures thereof.

3. The method of claim 1, wherein the method can detect substituted aromatic pollutant at about 0.1 ppm in the water sample.

4. The method of claim 1, wherein the comparing step is executed on a computer.

5. The method of claim 1, wherein the representative spectra is stored on a computer readable media.

* * * * *

UNITED STATES PATENT AND TRADEMARK OFFICE
CERTIFICATE OF CORRECTION

| | | |
|---|---|---|
| PATENT NO. | : 8,687,188 B2 | Page 1 of 1 |
| APPLICATION NO. | : 13/811609 | |
| DATED | : April 1, 2014 | |
| INVENTOR(S) | : Long et al. | |

It is certified that error appears in the above-identified patent and that said Letters Patent is hereby corrected as shown below:

On the Title Page

On Page 2, in item (56), under "OTHER PUBLICATIONS", in Column 1, Line 46, delete "Comtaminated" and insert -- Contaminated --, therefor.

In the Specification

In Column 12, Line 20, delete "and or" and insert -- and/or --, therefor.

In Column 13, Line 53, delete "and or" and insert -- and/or --, therefor.

In Column 15, Line 25, delete "of The" and insert -- of. The --, therefor.

In Column 16, Line 35, delete "SEAS" and insert -- SERS --, therefor.

Signed and Sealed this
Twenty-sixth Day of August, 2014

Michelle K. Lee
*Deputy Director of the United States Patent and Trademark Office*